United States Patent
Zhang et al.

(10) Patent No.: US 7,472,597 B2
(45) Date of Patent: Jan. 6, 2009

(54) ULTRASONIC IMAGING DEVICE AND THE INFORMATION PROCESSING METHOD THEREOF

(75) Inventors: Liguo Zhang, Nanshan (CN); Zhiyong Guan, Nanshan (CN); Xujin He, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 395 days.

(21) Appl. No.: 11/323,087

(22) Filed: Dec. 30, 2005

(65) Prior Publication Data

US 2006/0288785 A1 Dec. 28, 2006

(30) Foreign Application Priority Data

Jun. 26, 2005 (CN) .................. 2005 1 0035602

(51) Int. Cl.
*G01S 15/00* (2006.01)
*A61B 8/14* (2006.01)

(52) U.S. Cl. .............. 73/606; 73/618; 73/626; 600/437; 600/443

(58) Field of Classification Search .......... 73/606, 73/596, 597, 618, 626; 600/437, 443, 447, 600/453, 455, 457, 448
See application file for complete search history.

(56) References Cited

U.S. PATENT DOCUMENTS

| | | | |
|---|---|---|---|
| 6,231,510 B1 * | 5/2001 | Negrin et al. .............. 600/443 |
| 6,468,217 B1 | 10/2002 | Faziolo |
| 6,475,146 B1 * | 11/2002 | Frelburger et al. .......... 600/437 |
| 6,638,227 B2 * | 10/2003 | Bae ............................ 600/443 |
| 6,771,822 B1 * | 8/2004 | Brackett ..................... 382/232 |
| 6,885,113 B2 * | 4/2005 | Lim ........................ 290/40 R |
| 2004/0028376 A1 * | 2/2004 | Maita ........................... 386/68 |
| 2005/0096539 A1 * | 5/2005 | Leibig et al. ................ 600/437 |
| 2007/0161898 A1 * | 7/2007 | Hao et al. ................... 600/443 |
| 2007/0167780 A1 * | 7/2007 | Imamura et al. ............ 600/443 |

FOREIGN PATENT DOCUMENTS

| | | |
|---|---|---|
| CN | 1296705 A | 5/2001 |
| CN | 1528243 A | 9/2004 |
| JP | 200527745 A | 2/2005 |

* cited by examiner

*Primary Examiner*—Hezron Williams
*Assistant Examiner*—J M Saint Surin
(74) *Attorney, Agent, or Firm*—Kory D. Christensen; Stoel Rives LLP

(57) ABSTRACT

An ultrasonic imaging device, comprising: a receiver, for receiving ultrasonic signals which carry information about human body; a processor, for analyzing and processing the received ultrasonic signals in order to get image and/or sound signals; a controller, for issuing at least one instruction; and a recorder, for recording the image and/or sound signals on recording medium in digital form in accordance with the instruction.

11 Claims, 3 Drawing Sheets

ULTRASONIC IMAGING DEVICE AND THE INFORMATION PROCESSING METHOD THEREOF

FIELD OF THE INVENTION

The invention relates to ultrasonic imaging device, in particular, relates to an ultrasonic imaging device which comprises integrated recording device, and the information processing method used in the ultrasonic imaging device.

DESCRIPTION OF THE RELATED ART

In medical ultrasonic systems, the ultrasonic signals which carry the information relating to human body should be recorded. FIG. 1 shows the ultrasonic system used on human body, comprising probe 101, ultrasonic transmitting unit 102, ultrasonic receiving unit 103, central control unit 104, control panel 105, beamformer 106, black and white image signal processing unit 107, color bloodstream signal processing unit 108, Doppler signal processing unit 109, scan-transforming unit 110, speaker 111 and display 112.

The probe 101 is a transducer of ultrasound, for transducing the electric power to sound power and vice versa. The ultrasonic transmitting unit 102 could generate a set of high voltage pulses in a specific timing. The high voltage pulses are transduced into ultrasonic waves entering into human body's tissue by probe 101. The ultrasonic waves reflected by the tissue are transuded into electric signals by probe 101. The ultrasonic receiving unit 103 processes the received electric signals for achieving high voltage isolation amplification and A/D conversion, and then sends the processed signals into beamformer 106 for synthesizing the beam. The synthesized back wave signals are sent into black and white image signal processing unit 107, color bloodstream processing unit 108 and Doppler signal processing unit 109 respectively, for analyzing and processing. The black and white image signal processing unit 107 renders the signals by brightness modulation, and outputs B mode image, M mode image, the color bloodstream signal processing unit 108 outputs color bloodstream image, the Doppler signal processing unit 109 renders the signals by using of Doppler frequency-shifting effects and outputs positive and negative direction sound signals of bloodstream besides the sound spectrum. The image signals output by above-mentioned three units are sent to scan-transforming unit 110, for producing image signals suit for displaying on display 112. The scan-transformed image signals are then sent into display 112 for displaying. The positive and negative direction sound signals of bloodstream produced by Doppler signal processing are sent into speaker 111, which converts the sound signals into audible sound signals for output. The central control unit 104 controls the operations of all the above-mentioned units. The control panel 105, display 112 and speaker 111 are the human-machine interface of the ultrasonic system. The control panel 105 is the input device of the ultrasonic system. The user could input control instructions and information etc. to central control unit by control panel 105. The display 112 is the output device of image, and the speaker 111 is the output device of sound. In order to record the processed image and/or sound signal, the ultrasonic system connects a VCR (not shown), which located outside the ultrasonic system, and sends the respective signals output by the three signal processing units into the external VCR for recording.

In the conventional ultrasonic systems, the VCR (Video Cassette Recorder) system is used for recording the image and sound signals captured by ultrasonic system, wherein, the VCR system is located outside the ultrasonic system. There are many disadvantages for recording image and sound signal of the ultrasonic system by external VCR. First, the analog recording used by VCR is subject to the influence of environment such that the reliability of the recording is low and does not suit for long time preservation. Second, the tapes serve as recording medium are expensive and the capacity thereof is small. Third, the external VCR takes up a lot of space, and could not operate conveniently.

SUMMARY OF THE INVENTION

In order to solve above-mentioned problems, the object of present invention is to provide an ultrasonic imaging device, which comprising the function of recording image and/or sound signal.

One aspect of present invention is to provide an ultrasonic imaging device, comprising: a receiver, for receiving ultrasonic signals which carry information about human body; a processor, for analyzing and processing the received ultrasonic signals in order to get image and/or sound signals; a controller, for issuing at least one instruction; a recorder, for recording the image and/or sound signals on recording medium in digital form in accordance with the instruction.

The other aspect of present invention is to provide an information processing method used for ultrasonic imaging device, including steps: (a) receiving the ultrasonic signals which carry information about human body; (b) analyzing and processing the received signals in order to get image and/or sound signals; (c) issuing at least one instruction; (d) recording the image and/or sound signals onto a recording medium in digital form in accordance with the instruction.

BRIEF DESCRIPTION OF THE DRAWINGS

The present invention will be described in detail with accompanied figures and the embodiments, wherein.

BEST MODE FOR CARRYING OUT THE INVENTION

The embodiments of present invention will be described in detail with accompanied figures.

Figure 1:
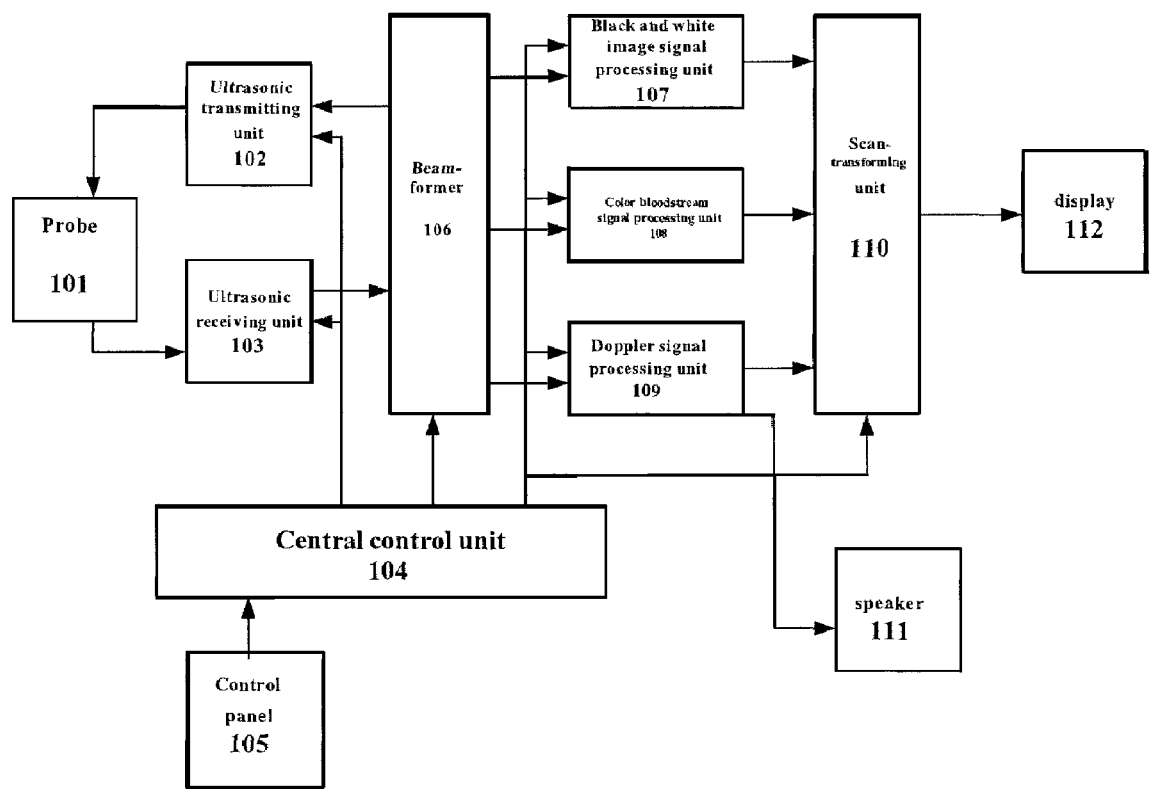
FIG. 1 shows the block gram of the ultrasonic system.
Figure 2:
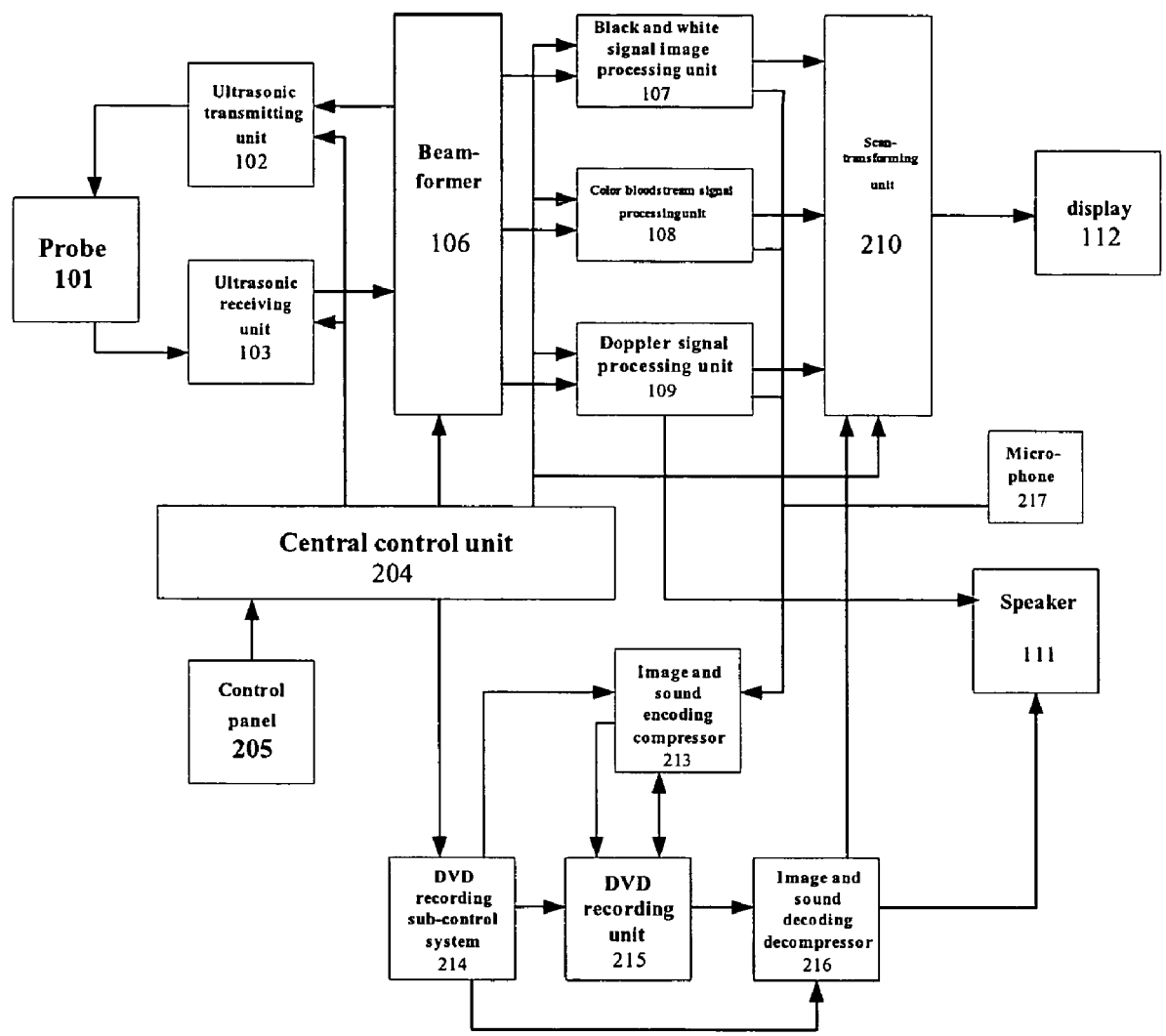
FIG. 2 shows the block gram of the ultrasonic imaging device of present invention.

FIG. 2 shows the structure of the ultrasonic imaging device of present invention, comprising: probe 101, ultrasonic transmitting unit 102, ultrasonic receiving unit 103, central control unit 204, control panel 205, beamformer 106, black and white image signal processing unit 107, color bloodstream signal processing unit 108, Doppler signal processing unit 109, scan-transforming unit 210, speaker 111, display 112, image and sound encoding compressor 213, DVD recording sub-control system 214, DVD recording unit 215, image and sound decoding decompressor 216 and microphone 217. The same units as those in FIG. 1 are assigned with the same reference numbers and the descriptions thereof are omitted.

In comparing with conventional ultrasonic systems, the ultrasonic imaging device of present invention further comprises a recording module for recording the image and/or sound signals onto a recording medium. The recording module encodes and compresses the image and/or sound signals produced by the ultrasonic device as well as the sound signals inputted from the microphone 217 in real-time by use of image and sound encoding compressor 213. Then the recording module sends the encoded and compressed image and/or sound signals as well as encoded and compressed sound signals which are input from the microphone into DVD recording unit 215 in accordance with the control of DVD recording sub-control unit 214. The encoded and compressed signals are then recorded onto recording medium.

Moreover, under the control of DVD recording sub-control unit 214, the DVD recording unit 215 could read the encoded and compressed image and/or sound signals from the recording medium, and send the signals to image and sound decoding decompressor 216 for decoding and decompressing. The decoded and decompressed image signals are then sent to scan-transforming unit 210 for the transformation from interleave scan to progressive scan. The scan-transformed image signals are combined with the display items of the ultrasonic system (such as menu, etc.), and are further displayed on the display 112 in a progressive way. The decoded and decompressed sound signals are playbacked by the speaker 111.

In the whole ultrasonic system, the control panel 205 and the microphone 217 are input devices. The users could input various instructions (such as record, playback, open, close, etc.) into central control unit 204 via the control panel 205. The control of operations of the ultrasonic system and the recording module are handled by central control unit 204. The central control unit 204 controls ultrasound transmitting and receiving, beamforming, signal processing and scan-transforming, etc. directly, and controls the recording module by sending instructions to DVD recording sub-control system 214. The user could input sound signals to the ultrasonic system via microphone 217 for recording.

The central control unit sends control instructions to DVD recording sub-control system 214, then the DVD recording sub-control system 214 parses the received instructions and generates corresponding commands to image and sound encoding compressor, image and sound decoding decompressor, DVD recording unit, respectively. Those components then operate according to the commands generated by DVD recording sub-control system 214.

The central control unit 204 communicates with DVD recording sub-control system 214 via serial communication protocol, which is suit for saving bit-width of the hardware. The length of control serial code could be determined depends on the number of the control instructions (such record, playback, open, close, etc.). The length of the control code (i.e. the number of the instructions) could be easily expanded and is not constrained by hardware, which is suit for the integration of the recording module.

It should be noted that, by using of other components, the present embodiment could be implemented in many other similar ways. The input device of the ultrasonic system could be the menu on the display, which could be operated to input various instructions. The central control unit could communicate with DVD recording sub-control system via other communication protocols, such as parallel communication protocol, etc. The signal processing unit could include separate M mode/B mode ultrasonic signal processing unit. The Doppler signal processing unit could include pulse wave and/or continuous wave Doppler ultrasonic signal processing unit. Moreover, the recording unit in present invention is not limit to DVD recording unit, any other recorder that could record data on recording medium, such as CD-ROM recorder, could be used as the recording unit.

Another embodiment of present invention will be described in reference to accompanied figures.

Figure 3:
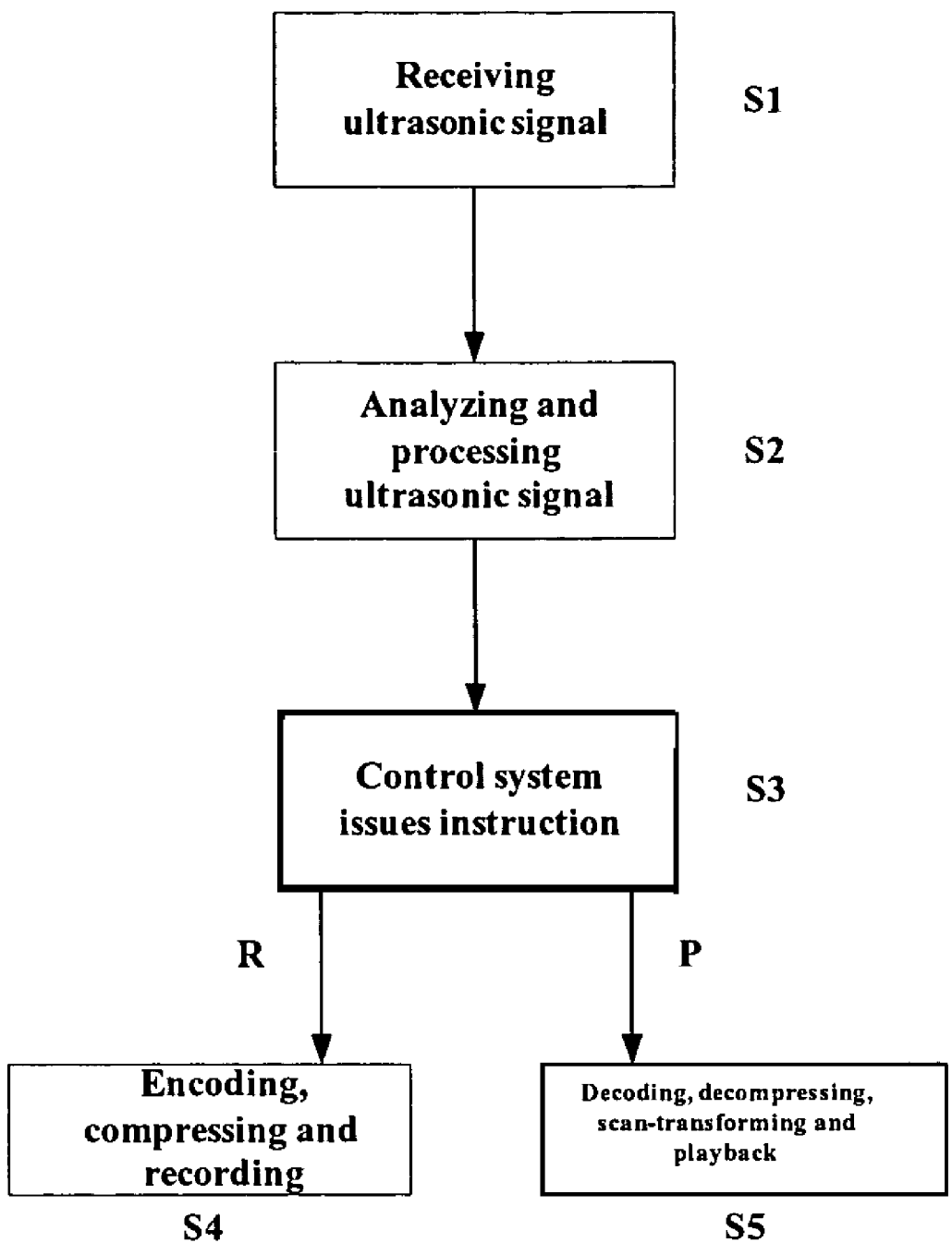
FIG. 3 is the flowchart of the information processing procedure of present invention.

FIG. 3 shows the flowchart of the information processing method of the invention.

In step S1, the ultrasonic receiving unit receives the ultrasonic signals which carry the information about human body. In step S2, the signal processing unit (such as black and white signal processing unit, etc.) analyzes and processes the received signals. In step S3, the control unit sends out the instruction for indicating the recording after encoding compression procedure or indicating the playback after decoding decompression procedure. If the instruction indicates encoding compression and recording (S3: R), the encoding compressor encodes and compresses the signals, then records the encoded signals in a digital form in step S4. If the instruction indicates decoding decompression and playback (S3: P), the decoding decompressor decodes and decompresses the signals, then scan-transforms the decoded signals in step S5, such that the signals which carry the information of human body could be displayed.

In the above-mentioned information processing method, the received and processed signals could be (but not limits to) M mode ultrasonic signals, B mode ultrasonic signals, C mode ultrasonic signals, CM mode ultrasonic signals and Doppler ultrasonic signals, etc.

By using of above-mentioned information processing method, the ultrasonic imaging device could achieve the recording of image and/or sound signals.

Although the invention is described by way of embodiments, it is understood by those skilled in the art that many modifications and changes could be made without departing from the essence of the spirit and scope of the appended claims.

ADVANTAGES OF THE INVENTION

The present invention further integrates recording function of image and/or sound signals in ultrasonic system without influences the performance of the ultrasonic system. The ultrasonic imaging device of the invention is highly integrated and easy to control. Moreover, the ultrasonic imaging device of the invention could records the image and sound signals on the medium which are good at preservation. The recording procedure could operate in real-time, such that the ultrasonic imaging device could be used widely in ultrasonic systems.

What is claimed is:

1. An ultrasonic imaging device, comprising:
   a receiver, for receiving ultrasonic signals which carry information about a human body;
   a processor, for analyzing and processing the received ultrasonic signals in order to obtain image and/or sound signals;
   a controller, for issuing at least one instruction;
   a recorder, for recording the image and/or sound signals on a recording medium in digital form in accordance with the instruction, wherein the recorder is integrated within the ultrasonic imaging device; and
   an encoding compressor, for encoding and compressing the image and/or sound signals in accordance with the instruction,
   wherein the recorder records the encoded and compressed signals onto the recording medium in accordance with the instruction.

2. The ultrasonic imaging device according to claim 1, further comprising:
   a decoding decompressor, for decoding and decompressing the digital signals in the recording medium in accordance with the instruction;
   an imaging device, for transforming the scan format of the decoded and decompressed signals in order to display the ultrasonic signals which carry information about human body on a display device.

3. The ultrasonic imaging device according to claim 2, wherein the processor comprises:
   a Doppler signal processing unit, for rendering the signals by use of Doppler frequency-shifting effects.

4. The ultrasonic imaging device according to claim 3, wherein the Doppler signal processing unit comprises:
   a pulse wave and/or continuous wave Doppler signal processing unit.

5. The ultrasonic imaging device according to claim 2, further comprising:
   a sound output device, for outputting the decoded and decompressed signals as audible sound signals.

6. The ultrasonic imaging device according to claim 1, wherein the processor comprises:
   M mode and/or B mode ultrasonic signals processing unit, for rendering the signals in a brightness modulation way.

7. The ultrasonic imaging device according to claim 1, further comprising:
   a sound input device, for transferring the received sound signals to the encoding compressor.

8. The ultrasonic imaging device according to claim 1, wherein, the controller issuing the instruction via serial communication protocol.

9. An information processing method for ultrasonic imaging device, comprising:
   (a) receiving the ultrasonic signals which carry information about human body;
   (b) analyzing and processing the received signals in order to obtain image and/or sound signals;
   (c) issuing at least one instruction;
   (d) recording the image and/or sound signals onto a recording medium in digital form in accordance with the instruction; and
   (e) encoding and compressing the image and/or sound signals in accordance with the instruction; wherein the encoded and compressed signal are recorded on the recording medium in accordance with the instruction.

10. The information processing method according to claim 9, further comprising:
    decoding and decompressing the digital signals in the recording medium in accordance with the instruction; and transforming the scan format of the decoded and decompressed signals in order to display the signals which carry information about human body.

11. The information processing method according to claim 10, wherein, in step (b), the received signals are at least one of M mode ultrasonic signal, B mode ultrasonic signal, C mode ultrasonic signal, CM mode ultrasonic signal and Doppler ultrasonic signal.

* * * * *